(12) United States Patent
Childers et al.

(10) Patent No.: US 7,160,425 B2
(45) Date of Patent: Jan. 9, 2007

(54) CELL TRANSPORTER FOR A BIODEVICE

(75) Inventors: Winthrop D. Childers, San Diego, CA (US); David Tyvoll, La Jolla, CA (US); Kirk Norton, San Diego, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 174 days.

(21) Appl. No.: 10/808,897

(22) Filed: Mar. 25, 2004

(65) Prior Publication Data

US 2005/0214736 A1 Sep. 29, 2005

(51) Int. Cl.
G01N 27/453 (2006.01)
C12M 1/00 (2006.01)

(52) U.S. Cl. .................... 204/643; 435/307.1
(58) Field of Classification Search ............... 204/643, 204/547; 435/307.1
See application file for complete search history.

(56) References Cited

U.S. PATENT DOCUMENTS

| | | | |
|---|---|---|---|
| 4,874,507 A | 10/1989 | Whitlock | |
| 4,911,806 A | 3/1990 | Hofmann | |
| 5,126,022 A | 6/1992 | Soane et al. | |
| 5,344,535 A | 9/1994 | Betts et al. | |
| 5,454,472 A | 10/1995 | Benecke et al. | |
| 5,489,506 A * | 2/1996 | Crane ........................ | 435/2 |
| 5,589,047 A | 12/1996 | Coster et al. | |
| 5,626,734 A | 5/1997 | Docoslis et al. | |
| 5,653,859 A | 8/1997 | Parton et al. | |
| 5,814,200 A | 9/1998 | Pethig et al. | |
| 5,858,192 A | 1/1999 | Becker et al. | |
| 5,938,904 A | 8/1999 | Bader et al. | |
| 5,993,630 A | 11/1999 | Becker et al. | |
| 5,993,631 A | 11/1999 | Parton et al. | |
| 5,993,632 A * | 11/1999 | Becker et al. ............... | 204/547 |
| 6,056,861 A | 5/2000 | Fuhr et al. | |
| 6,059,950 A | 5/2000 | Dames et al. | |
| 6,149,789 A | 11/2000 | Benecke et al. | |
| 6,193,866 B1 | 2/2001 | Bader et al. | |
| 6,197,176 B1 | 3/2001 | Pethig et al. | |
| 6,264,815 B1 | 7/2001 | Pethig et al. | |
| 6,287,832 B1 | 9/2001 | Becker et al. | |
| 6,306,272 B1 | 10/2001 | Soane et al. | |
| 6,310,309 B1 | 10/2001 | Ager et al. | |
| 6,403,367 B1 | 6/2002 | Cheng et al. | |
| 6,465,225 B1 | 10/2002 | Fuhr et al. | |
| 6,537,433 B1 | 3/2003 | Bryning et al. | |
| 6,540,895 B1 | 4/2003 | Spence et al. | |
| 6,596,143 B1 | 7/2003 | Wang et al. | |
| 6,610,188 B1 | 8/2003 | Fuhr et al. | |
| 6,641,708 B1 | 11/2003 | Becker et al. | |
| 6,660,493 B1 | 12/2003 | Miles | |

(Continued)

FOREIGN PATENT DOCUMENTS

WO    WO 97/34689    9/1997

(Continued)

OTHER PUBLICATIONS

Tsuda, Takao, Yamauchi, Norihiro, and Kitagawa, Shinya, "Separation of Red Blood Cells at the Single Cell Level by Capillary Zone Electrophoresis", Analytical Sciences, vol. 16, pp. 847-850, (Aug. 2000).

(Continued)

*Primary Examiner*—Alex Noguerola (57) ABSTRACT

A method of transporting cells comprising transporting a plurality of cells through a transport path of a biodevice and maintaining substantially free individual movement of each cell during the transporting of the cells through the transport path.

26 Claims, 6 Drawing Sheets

U.S. PATENT DOCUMENTS

| | | | |
|---|---|---|---|
| 6,673,225 | B1 | 1/2004 | Arnold |
| 6,685,812 | B1 | 2/2004 | Miles |
| 6,727,451 | B1 | 4/2004 | Fuhr et al. |
| 6,730,204 | B1 | 5/2004 | Mariella, Jr. |
| 6,749,736 | B1 | 6/2004 | Fuhr et al. |
| 6,761,811 | B1 | 7/2004 | Mariella, Jr. |
| 6,881,314 | B1 * | 4/2005 | Wang et al. .......... 204/600 |
| 2002/0005354 | A1 | 1/2002 | Spence et al. |
| 2002/0036141 | A1 | 3/2002 | Gascoyne et al. |
| 2002/0042125 | A1 | 4/2002 | Peterson et al. |
| 2002/0055167 | A1 | 5/2002 | Pourahmadi et al. |
| 2002/0076825 | A1 | 6/2002 | Cheng et al. |
| 2002/0182627 | A1 | 12/2002 | Wang et al. |
| 2002/0182654 | A1 | 12/2002 | Jing et al. |
| 2003/0010637 | A1 | 1/2003 | Cummings |
| 2003/0121788 | A1 | 7/2003 | Gascoyne et al. |
| 2003/0134416 | A1 | 7/2003 | Yamanishi et al. |
| 2003/0159932 | A1 | 8/2003 | Betts et al. |
| 2004/0011652 | A1 | 1/2004 | Bressler |

FOREIGN PATENT DOCUMENTS

| | | |
|---|---|---|
| WO | WO 98/10869 | 3/1998 |
| WO | WO-01/05514 A1 * | 1/2001 |
| WO | WO 02/12896 | 2/2002 |
| WO | WO 02/12896 A1 | 2/2002 |
| WO | WO 02/28523 | 4/2002 |
| WO | WO 03/014291 | 2/2003 |
| WO | WO 03/093496 | 11/2003 |
| WO | WO 2004/050252 A1 | 6/2004 |

OTHER PUBLICATIONS

Holmes, David and Morgan, Hywel, "Cell Positioning and Sorting Using Dielectrophoresis", European Cells and Materials, vol. 4, Suppl. 2, pp. 120-122, (2000).

Swiss Center for Electronics and Microtechnology, "Dielectrophoretic Size-Sensitive Particle Filter for Micro-Fluidic Applications", 2 pgs., printed Feb. 24, 2004 from www.csern.ch/corporate/Report2002/pdf/microbotics.pdf.

* cited by examiner

CELL TRANSPORTER FOR A BIODEVICE

CROSS-REFERENCE TO RELATED APPLICATIONS

This application is related to U.S. patent application Ser. No. 10/808,945, entitled "METHOD OF SORTING CELLS ON A BIODEVICE", and U.S. patent application Ser. No. 10/808,803, entitled "METHOD OF SORTING CELLS IN SERIES", both filed on even date herewith, assigned to the assignee of the present application, and incorporated herein by reference.

BACKGROUND

The rapid miniaturization in electronic devices, particularly their manufacture and assembly, has transformed the medical industry. In particular, handling and testing of cells and other components within body fluids has moved beyond the conventional test tube to other devices, such as biochips. A biochip, sometimes called a lab-on-a-chip, refers to placement of biologic materials on a miniature electronic device capable of electrically and/or chemically interacting with the biologic materials for testing or other purposes.

Considerable efforts have been made in the biochip environment to apply electric fields to manipulate cells, including their movement, separation, property determination, etc. Despite numerous attempts at cell manipulation with electric fields, the ability to manipulate cells is still limited by different characteristics of the cells, such as cell size, cell aggregation, cell polarizability, etc. For example, the tendency of cells to aggregate is exhibited during attempts to transport the cells. Impeding transportation of the cells on the biochip, in turn, hampers the ability to perform other functions with the cells (e.g., sorting, separation, isolation, analyte tests, etc.) on the biochip.

For these reasons, among others, widespread use of biochip devices has been limited.

DETAILED DESCRIPTION

In the following detailed description, reference is made to the accompanying drawings which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments of the present invention can be positioned in a number of different orientations, the directional terminology is used for purposes of illustration and is in no way limiting. It is to be understood that other embodiments may be utilized and structural or logical changes may be made without departing from the scope of the present invention. Finally, although a flow chart in the figures of this application shows a specific order of execution, the order of execution may differ from that which is depicted. The following detailed description, therefore, is not to be taken in a limiting sense, and the scope of the present invention is defined by the appended claims.

Embodiments of the present invention are directed to a method for transporting cells on a biodevice while preventing aggregation of the cells during transport. The biodevice is a miniature stand-alone electronic device (such as a biochip) used for performing operations on biologic materials, such as separating and/or testing cells, and includes a mechanism for transporting cells between stations on the biodevice for separation, collecting, and/or testing of cells. The biodevice comprises an anti-aggregation mechanism which counters or prevents aggregation of the cells during their transport between other operative portions of the biodevice (e.g. stations for separation, collecting, and/or testing) so that the cells arrive at these stations in a non-aggregated state. The transporting mechanism and anti-aggregation mechanism are used in a transport path of the biodevice (i.e. a portion of the biodevice in which no other functions operate on the cell, such as sorting, filtering, testing, etc. during transport). Accordingly, the anti-aggregation mechanism does not act to permanently separate cells (or cell groups) from each other, or to isolate a cell or cell type from another cell type. Rather, the anti-aggregation mechanism facilitates a free flow of cells individually so that when the cells arrive at their destination (e.g. a next station/function of the biodevice), each cell is freely available relative to the other cells, thereby enhancing whatever operation is to be performed on the cell.

The transport mechanism of the biodevice imparts a primary motion of the cells along a transport path on the biodevice during a transport time period. This primary motion is implemented by a fluid flow pressure drop along the transport path or by application of a traveling wave dielectrophoretic field that induces cell motion along the transport path. This dielectrophoretic field is applied via one or more electrode arrays disposed on the biodevice along the transport path, and is described in more detail below.

The anti-aggregation mechanism of the biodevice imparts a secondary motion of the cells during transport of the cells. The secondary motion is one or more directional movements of a cell or particle in a direction generally different than the directional movement in the primary motion, and of a distance and magnitude so that the secondary motion does not impede the primary motion of the cells. In particular, while the distance that each cell moves by this secondary motion is relatively small relative to the distance moved via the primary transport motion, the magnitude of movement for each cell in the secondary motion is generally sufficient to discourage or counteract forces of attraction and adhesion between cells that otherwise causes aggregation of the cells. Generally speaking, the function of the secondary motion is either to initially break the adhesion or aggregation between cells or to avoid aggregation of already dispersed cells. The secondary motion moves each cell in a rapid manner that is regular or repeated so that it becomes difficult for the cells to aggregate together and adhere to each other. In some embodiments, this secondary motion can be agitative, i.e., a rapid motion of each cell that is irregular (but limited) in its magnitude, distance, and/or direction.

The secondary motion caused by the anti-aggregation mechanism is implemented via an electric field, acoustic waves, or ultrasonic waves to apply a rotational force, vibratory force, centering force, etc. The electric field applied by the anti-aggregation mechanism is applied by an electrode arrangement that imparts an electrorotational effect on the cells and/or imparts a dielectrophoretic field on the cells, which is further described below.

Each of these forces can be applied with a sufficiently high magnitude to cause the de-aggregation effect yet not disrupt the primary motion of the cell because of nature of the force applied, as well as the capability of a signal generator to control parameters of the secondary motion. For example, the signal generator can rapidly change the polarity/phase of the signals generating these fields to alter the directional movements and distances traveled by each cell in the secondary motion. Finally, directional movements of cells in the secondary motion can be two-dimensional within a plane, but also can be three-dimensional (e.g. along three axes of movement).

A dielectrophoretic field can be applied by the biodevice to impart the primary motion (via the transport mechanism) and/or the secondary motion (via the anti-aggregation mechanism). This dielectrophoretic field can be defined as an electric field that varies spatially or is non-uniform where it is being applied to the particles (e.g. cells). Positive dielectrophoresis occurs when the particle (e.g. cell) is more polarizable than the medium (e.g. plasma) and results in the particle being drawn toward a region of higher field strength. A system operating in this way can be referred to as operating in a positive dielectrophoresis mode. Negative dielectrophoresis occurs when the particle is less polarizable than the medium and results in the particle being drawn toward a region of lesser field strength. A system operating in this way can be referred to as operating in a negative dielectrophoresis mode.

First, these electric fields are generated by applying a voltage between two or more electrodes. The field electrodes are disposed and arranged in a geometric relationship relative to one another to cause a non-uniformity or spatial variation in the applied electric field, which produces the dielectrophoretic effect. Accordingly, selectively applied variations in this geometric relationship of the field electrodes are used to cause desired movements of cells within the dielectrophoretic fields.

Second, by applying a time varying voltage to the field electrodes, a temporally varying electric field can be produced. This time variation will tend to affect the polarization of the fluid medium and the particles differently—hence it will affect the relative polarization between the fluid medium and the particles. Accordingly, selective application of time variance in the dielectophoretic field can be used to move cell particles in a desired manner.

In many cases, particularly where the variation is sinusoidal, the time variation has a characteristic frequency. The relative polarization of a particle relative to the medium is typically affected by the applied frequency. Large changes in frequency can be sufficient to change a system from operating in a negative dielectrophoresis mode to a positive dielectrophoresis mode. For example, there may be one frequency wherein the cells move toward regions of higher field strength (the positive dielectrophoresis mode) and another frequency wherein the cells move away from regions of higher field strength (the negative dielectrophoresis mode). Either negative or positive dielectrophoresis may be used in the embodiments of the present invention to move cells within a fluid medium such as a buffer or plasma.

Third, when using more than two field electrodes, certain types of motion can be induced by selectively shifting which pair of electrodes has a voltage difference or using an amplitude modulation technique. For example, an arrangement of four interleaved and independent field electrodes can induce a "traveling wave dielectrophoresis" response in the particles to allow controlled translation of the particles. This "traveling wave" effect is used to impart the primary motion for transporting cells or particles through a transporter of a biodevice.

The operation of the transport mechanism and the anti-aggregation mechanism is controlled by a transport control unit or controller. The transport control unit directs activation and deactivation of the transport mechanism and the anti-aggregation mechanism, either simultaneously or alternately, in time periods that can vary in duration to achieve a desired combination of the primary motion and the secondary motion.

Figure 1:
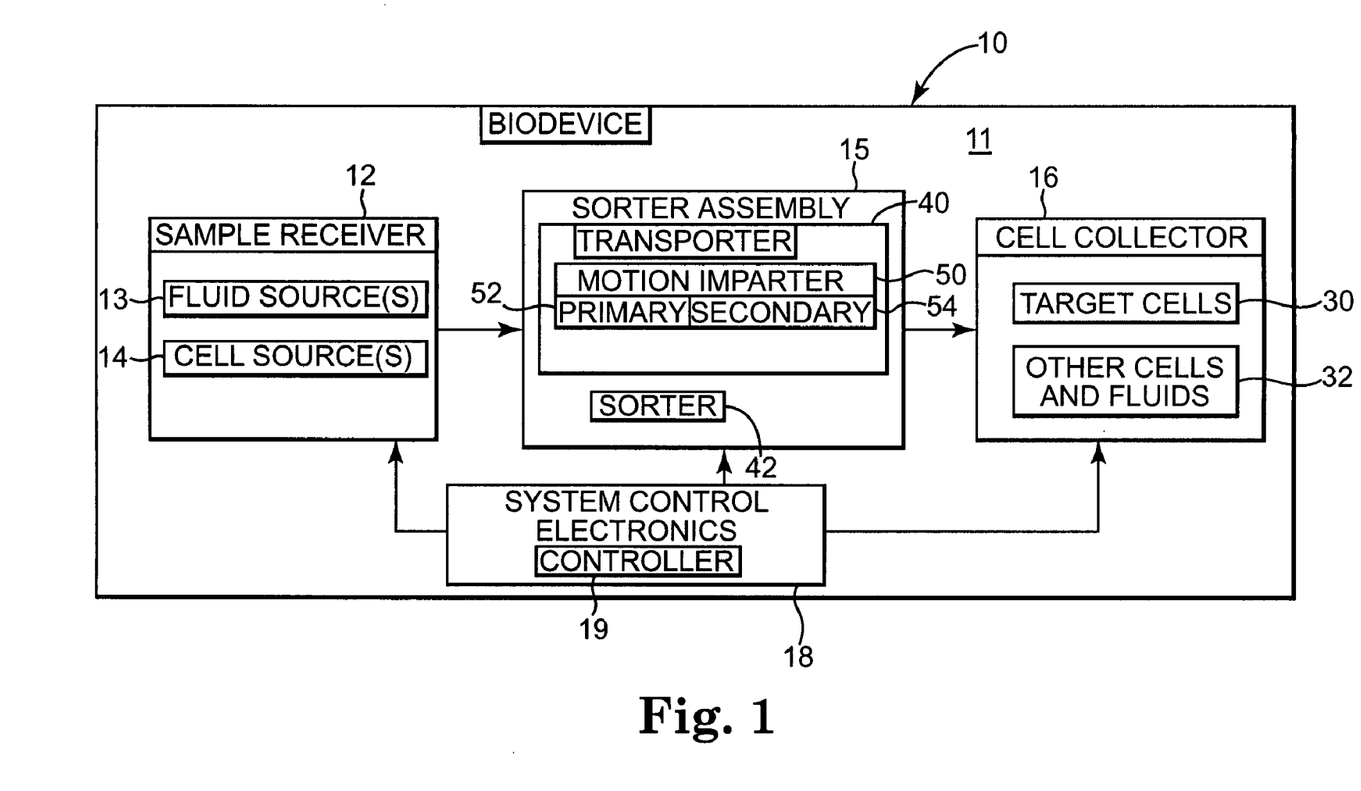
FIG. 1 is a block diagram of a biodevice, according to an embodiment of the present invention.

In one embodiment shown in FIG. 1, biodevice 10 is directed to receive a sample of cells within a fluid, transport and sort the cells, and then collect the cells as target cells and other cells (e.g., non-target cells). As shown in FIG. 1, biodevice 10 comprises sample receiver 12, sorter assembly 15, cell collector 16, and system control electronics 18 with controller 19. Sorter assembly 15 comprises transporter 40 and sorter 42. Transporter 40 of sorter assembly 15 comprises motion imparter 50 with primary motion imparter 52 and secondary motion imparter 54. Cell collector 16 comprises target cells 30 and other cells/fluids 32.

System control electronics 18 of biodevice 10 is in electrical communication with sample receiver 12, sorter assembly 15, and cell collector 16. System control electronics 18 directs various functions of biodevice 10 including operation of controller 19 which is configured to direct various electric, acoustic, ultrasonic fields/forces to be applied by transporter 40. As further described in association with FIG. 2, controller 19 comprises a waveform generator that enables waveforms (temporally varying and non-temporally varying) that are operable at selectable magnitudes (e.g., voltages), frequencies, phases, and polarities (e.g., negative or positive frequencies). In some embodiments, this waveform generator is capable of generating signal frequencies in the range from DC to several GHz.

Sample receiver 12 of biodevice 10 comprises fluid source(s) 13 and cell source(s) 14. Fluid source(s) 13 receive one or more types of fluid and/or fluid mediums for use on biodevice 10 while cell source(s) 14 receive one or more types of cells suitable for handling and testing on biodevice 10. Fluid source(s) 13 of biodevice 10 include, but are not limited to, one or more sources of fluid mediums, such as fluid suspensions, blood and blood derivatives, reagent solutions, etc. Cell source(s) 14 within biodevice 10 include, but are not limited to, one or more sources of cells, such as human cells, animal cells, etc, as well as other particles, such as cell organelles, analytes, bacteria, viruses, etc, including combinations of the same. In some embodiments, cell source(s) 14 also comprise other particles such as molecules that tend to aggregate together and which would exhibit a tendency to aggregate when being transported on a biodevice.

Sorter 42 of sorter assembly 15 comprises any one or more particle sorting modules configured for separating different types of particles from each other, as well as from a fluid medium carrying the particles. In some embodiments, sorter 42 also comprises other functions and stations such as filtering, testing, focusing, isolating, or other operations suitable for performing functions on biologic materials on a biodevice.

Transporter 40 of sorter assembly 15 comprises a motion imparter 50 configured to move cells within a fluid medium, while preventing unintentional aggregation of the cells, from a first location on biodevice 10 to a second location on biodevice 10. These first and second locations, as well as others, are represented by sorter 42. Primary motion imparter 52 acts to move the cells through transporter 40 while second motion imparter 54 acts to cause secondary motion in the cells during their primary movement to counteract a tendency of the cells to aggregate together.

Cell collector 16 collects target cells 30 and other cells 32 (e.g. non-target cells) as a result of the operation of sorter assembly 15 on fluid/cell sample from sample receiver 12.

Figure 2:
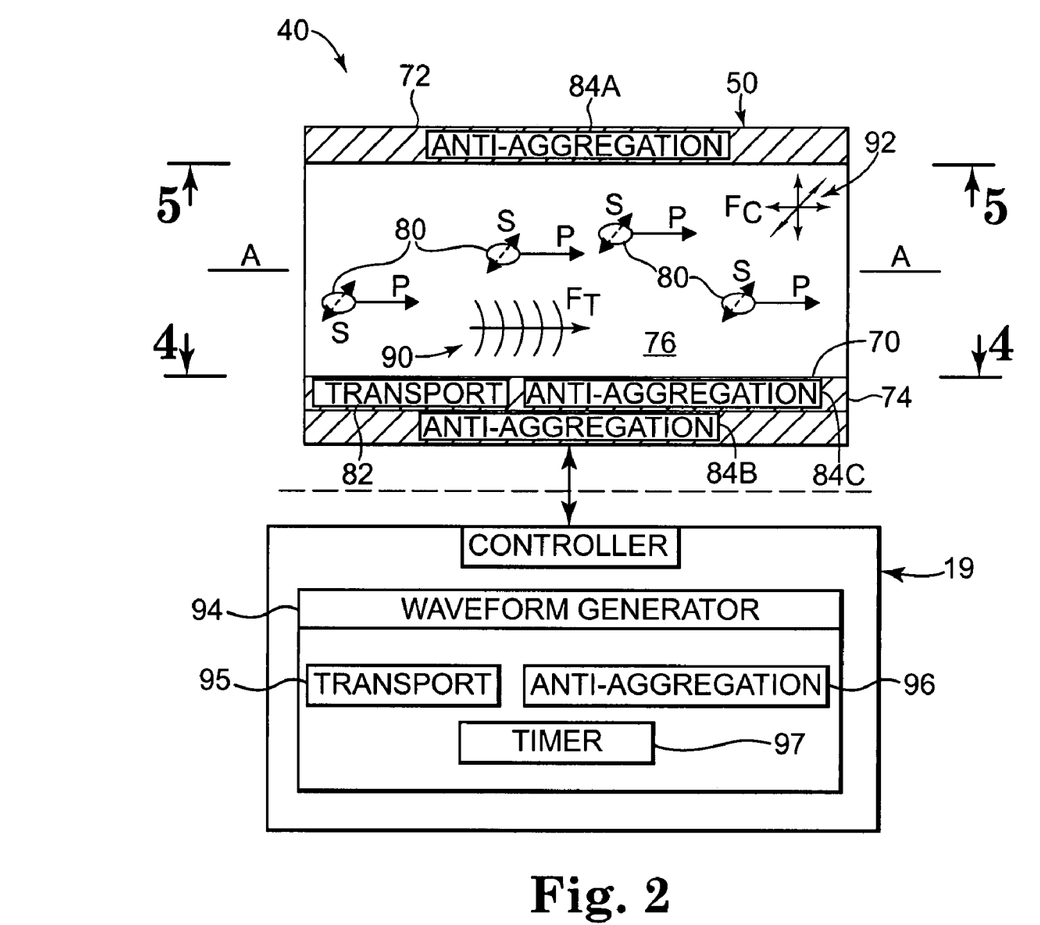
FIG. 2 is a schematic illustration of a cell transporter of a biodevice with partial sectional views and block diagrams, according to an embodiment of the present invention.

FIG. 2 illustrates one embodiment of transporter 40 of biodevice 10. As shown in FIG. 2, transporter 40 comprises motion imparter 50 which acts in cooperation with controller 19 of system control electronics 18 (FIG. 1). Motion imparter 50 comprises conduit 70 (e.g. a transport path), defined by first substrate 72 and second substrate 74, for carrying cells 80 within fluid medium 76. For illustrative purposes, each cell 80 is shown as having a primary motion indicated by directional arrow P and a secondary motion indicated by directional arrow S. Primary motion P reflects the movement of cells 80 through conduit 70 in a direction that is generally parallel to longitudinal axis A of transporter 40. Secondary motion S reflects the movement of cells 80 in direction(s) and/or orientation(s), other than the primary motion P, such as rotational and/or vibratory movements.

Transport mechanism 82 is contained within second substrate 74 and imparts the primary motion via application of a transport force (represented by the directional arrow $F_T$) in electric field 90. This electric field is a traveling wave dielectrophoretic field, as previously described. Transport mechanism 82 can be implemented in several ways, as further described in association with FIGS. 4–11.

Anti-aggregation mechanism 84 (shown as 84A, 84B, and/or 84C) imparts a secondary motion to cells 80, which counteracts a tendency of cells 80 to aggregate together during transport. Anti-aggregation mechanism 84 applies a three-dimensional force array 92 via an electric field, an ultrasonic wave, and/or an acoustic wave to impart the secondary motion. Anti-aggregation mechanism 84 can be implemented in first substrate 72 as an anti-aggregation mechanism 84A disposed vertically above and spaced from transport mechanism 82. In some embodiments, anti-aggregation mechanism 84 is disposed in second substrate 74 below transport mechanism 82 as anti-aggregation mechanism 84B. In other embodiments, anti-aggregation mechanism 84 is implemented as anti-aggregation mechanism 84C, which is disposed in bottom substrate 74 alongside or in combination with transport mechanism 82 in generally the same plane as transport mechanism 82. Finally, more than one of anti-aggregation mechanisms 84A, 84B, 84C can be implemented in a single embodiment. Implementation of anti-aggregation mechanisms 84A, 84B, and 84C are later described in more detail in association with FIGS. 4–11.

As further shown in FIG. 2, controller 19 of system control electronics 18 (FIG. 1) comprises waveform generator 94 having transport module 95, anti-aggregation module 96, and timer 97. Transport module 95 of signal generator 94 is configured to generate a waveform suited for inducing primary motion P while anti-aggregation module 96 is configured to generate physical fields for inducing secondary motion S to counteract aggregation of cells during transport. Controller 19 also comprises timer 97, which enables selective activation and deactivation of transport module 95 and anti-aggregation module 96 so that modules 95, 96 can operate simultaneously or alternately relative to each other. The operational modes controlled via timer 97 of controller 19 are later described in greater detail in association with FIG. 9.

As shown in FIG. 2, in use, transporter 40 of biodevice 10 drives cells 80 in a primary motion P through conduit 70 by application of transport Force $F_T$ generated by transport mechanism 82. During this cell transport, one or more of anti-aggregation mechanisms 84A, 84B, 84C are deployed to impart a secondary motion S in cells 80 to prevent their aggregation during transport. Embodiments of transport mechanism 82 and anti-aggregation mechanisms 84A, 84B, 84C are described in greater detail in association with FIGS. 4–11.

Figure 3:
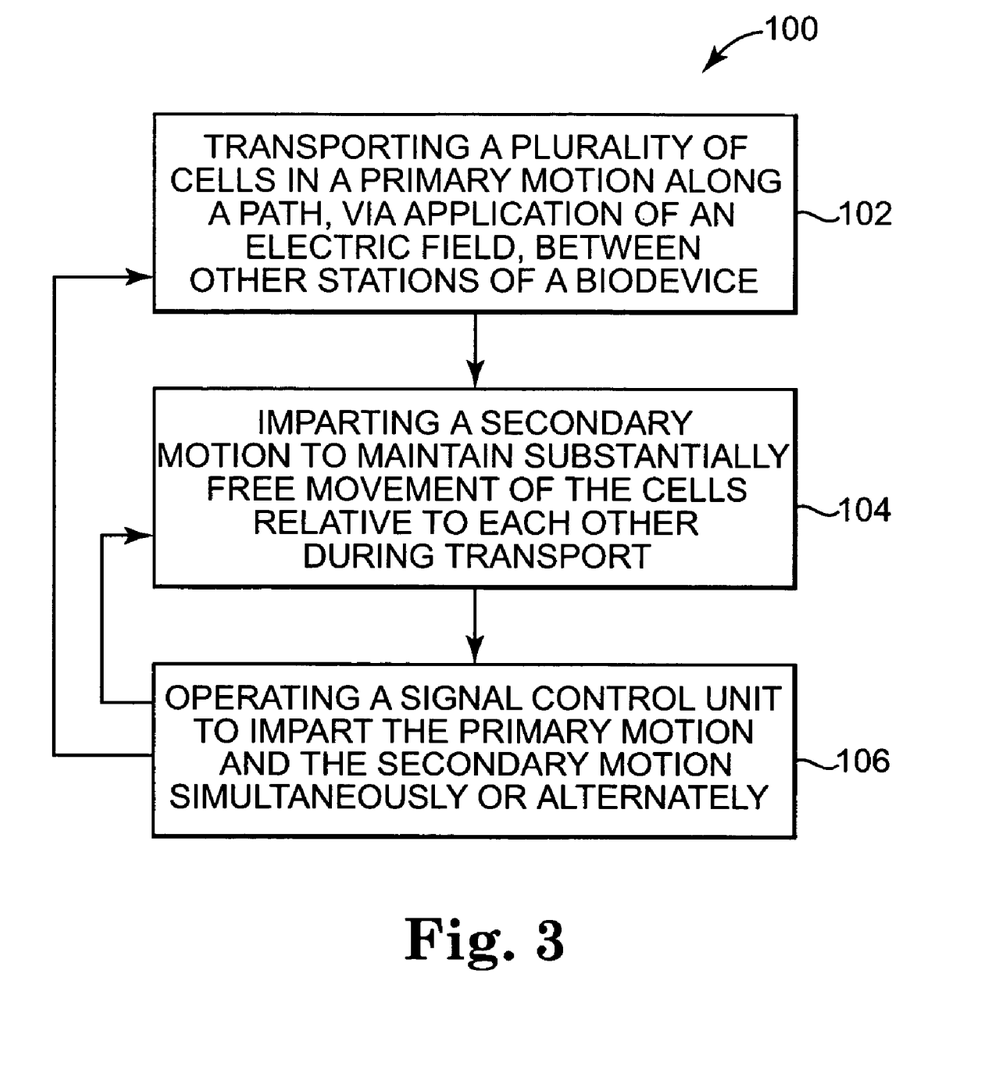
FIG. 3 is block diagram of a method of cell transport, according to an embodiment of the present invention.

FIG. 3 is a flow diagram of method 100 directed to substantially aggregation-free transport of cells on a biodevice between other functions or stations of the biodevice, such as cell separation, cell filtering, cell testing, etc. The systems and devices described in association with FIGS. 1–2, 4–10 are suitable for performing method 100.

As shown in box 102 of FIG. 3, method 100 comprises transporting a plurality of cells in a primary motion along a path, via application of an electric field, between other stations/functions of the biodevice. In one embodiment, the primary motion is achieved by applying a fluid flow pressure drop in combination with the electric field to move the cells. In other embodiments, the primary motion is applied solely by the fluid flow pressure drop, without the electric field.

Method 100 also comprises, as shown in box 104, imparting a secondary motion to the cells to maintain substantially free movement of the cells relative to each other during transport in the primary motion. As shown in box 106, method 100 also comprises operating a signal control unit to simultaneously or alternately impart the primary motion and the secondary motion to the cells.

FIGS. 4–11 illustrate various combinations of electrode arrays and/or elements along with other devices (e.g. ultrasonic device) for imparting a primary motion and/or a secondary motion to transport cells in a relatively aggregation-free manner along a transport path of a biodevice.

Figure 4:
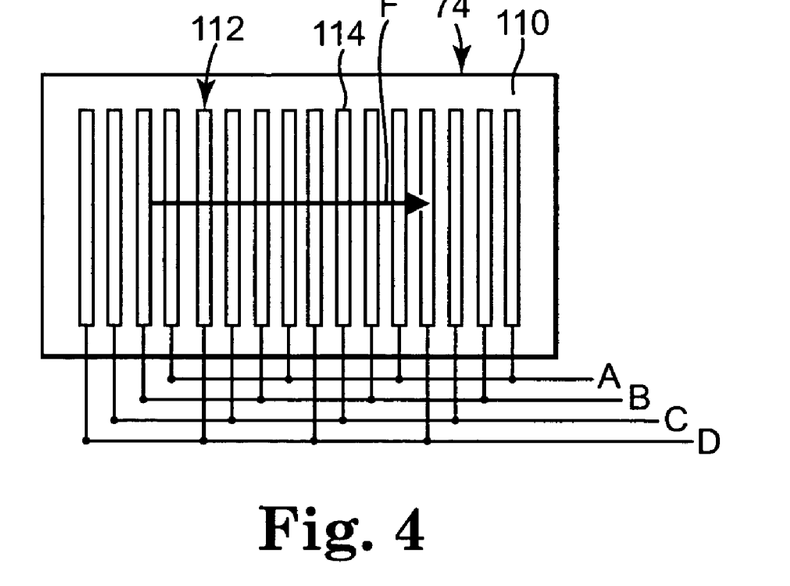
FIG. 4 is a sectional view of a cell transporter as taken along lines 4—4 of FIG. 2, according to an embodiment of the present invention.

FIG. 4 is a sectional view of transporter 40 of FIG. 2 looking at a surface of second substrate 74, and illustrates one embodiment of transport mechanism 82 of second substrate 74 (FIG. 2). As shown in FIG. 4, second substrate 74 comprises surface 110 and electrode array 112 of electrically conductive elements 114, which acts as transport mechanism 82. Electrode array 112 is configured to apply an electric field to cells 80 within fluid 76 (FIG. 2), and in particular, a traveling wave dielectrophoretic field to cells 80 to impart the primary motion P to move cells 80 generally parallel to directional force arrow F.

As shown in FIG. 4, electrode array 112 comprises a linear arrangement of electrode elements 114. In some embodiments, elements 114 of array 112 are arranged in an interleaved or interdigitated pattern. In some embodiments, electrode array 112 is exposed on surface 110 of second substrate 74, while in other embodiments, electrode array 112 is disposed just below surface 110 of second substrate 74.

Electrode array 112 is configured to apply the previously described dielectrophoretic field as a traveling wave to move these cells or particles substantially the whole length of second substrate 74. In one embodiment, electrode array 112 is used to achieve this traveling wave effect by linking every fourth electrode element together to form a signal channel (e.g. channel A) to permit activating and deactivating those linked elements together as a single unit. By repeating this arrangement, all of the electrode elements 114 are distributed into four operational sets in which each set defines a channel to enable four distinct signal channels (e.g., channels A, B, C, D) to be applied to electrode array 112 for implementing independent driving of each of the four operational sets. In this manner, electrode array 112 enables application of a traveling wave in a spatially varying electric field to impart a primary motion on cells 80 through conduit 70 of transporter 40 of biodevice 10 (FIG. 2).

Figure 5:
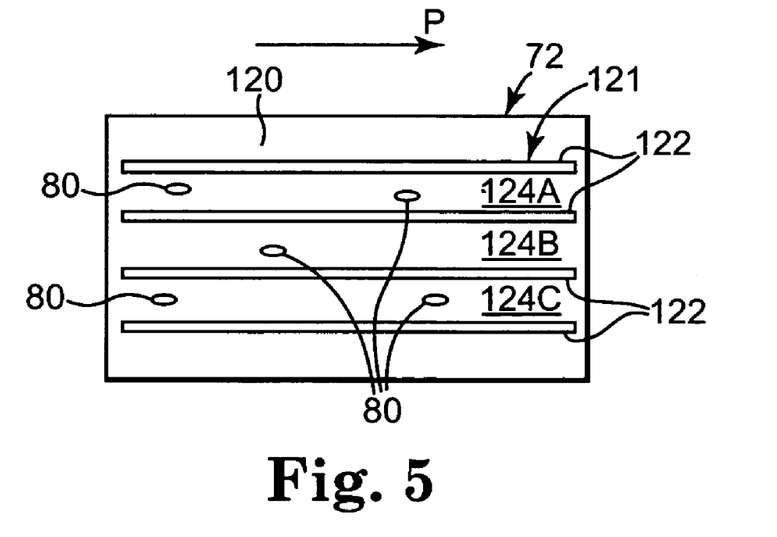
FIG. 5 is sectional view of a cell transporter as taken along lines 5—5 of FIG. 2, according to an embodiment of the present invention.

FIG. 5 is a sectional view of transporter 40 of FIG. 2 and schematically illustrates one embodiment of anti-aggregation mechanism 84. In particular, FIG. 5 shows an embodiment of transporter 40 which corresponds to anti-aggregation mechanism 84A being disposed in first substrate 72 vertically above and spaced from transport mechanism 82 in second substrate 74.

As shown in FIG. 5, first substrate 72 comprises surface 120 with array 121 of electrode elements 122 acting as anti-aggregation mechanism 84A (FIG. 2). Electrode elements 122 of array 121 are arranged generally parallel to each other and generally parallel to a longitudinal axis of first substrate 72. By application of a negative dielectrophoretic field between respective elements 122, cells 80 are moved in a secondary motion away from elements 122 to be maintained in one of channels 124A, 124B, and 124C, thereby preventing aggregation of cells 80 as they travel in the direction of primary motion P. In other words, the negative dielectrophoretic field applied via electrode array 120 causes a secondary motion in cells 80 that is transverse to the primary motion P, and tends to center cells 80 within each channel 124A, 124B, 124C.

In this embodiment, a free movement of cells 80 is maintained during transport by causing cells 80 to travel independent parallel paths (defined by elements 122) through transporter 40 (FIG. 2). In addition, more than three channels 124A, 124B, 124C can be defined by adding additional elements 122 to increase the number of independent parallel paths for cells 80 to travel, thereby increasing the opportunities for preventing aggregation of cells 80 during their transport.

In one embodiment, channels 124A, 124B, 124C are not physical channels in which walls physically separate respective cells, but rather are virtual channels in which cells 80 are constrained to stay between respective elements 122 primarily by the negative dielectrophoretic field, as if physical walls were there. In these embodiments, electrode elements 122 can be disposed just below surface 120. In other embodiments, these channels 124A, 124B, 124C are defined by electrode elements 122 and also act as physical boundaries, such as when electrode elements 122 are raised from surface 120.

Accordingly, one embodiment of transporter 40 of biodevice 10 (FIG. 2) comprises transport mechanism 82 for imparting a primary motion on cells 80, as shown in FIG. 4, in combination with anti-aggregation mechanism 84A for imparting a secondary motion on cells 80, as shown in FIG. 5.

Figure 6:
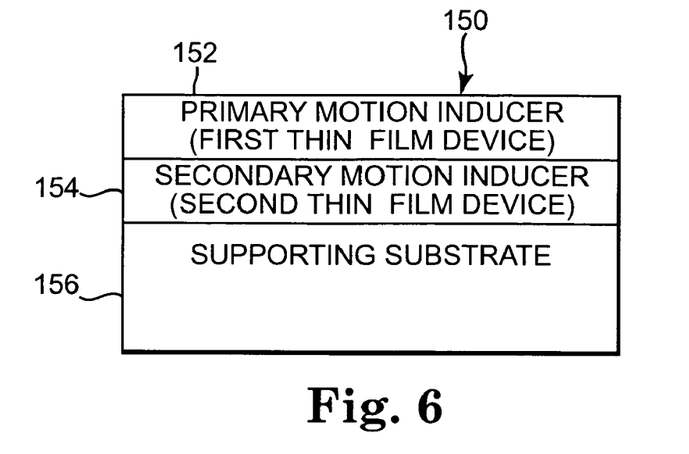
FIG. 6 is a schematic illustration of another cell transporter, according to an embodiment of the present invention.

FIG. 6 illustrates another embodiment of transporter 40 of biodevice 10 (FIG. 2) which corresponds to the embodiment shown in FIG. 2 of anti-aggregation mechanism 84B (for imparting a secondary de-aggregation motion on cells 80) being disposed beneath transport mechanism 82 for imparting a primary transport motion on cells 80. As shown in FIG. 6, transporter 150 comprises primary motion inducer 152, secondary motion inducer 154, and supporting substrate 156. Primary motion inducer 152 comprises a first thin film device overlayed onto secondary motion inducer 154, which comprises a second thin film device.

In some embodiments, transporter 40 of biodevice 10 (FIG. 1) is constructed as a substrate with one or more layers of thin film metallization of conductive components such as primary motion inducer 152 and secondary motion inducer 154, shown in FIG. 6.

In other embodiments, transporter 40 of biodevice 10 (FIG. 1) is constructed using semiconductor microfabrication techniques. For example, substrate 156 of transporter 40, as shown in FIG. 6, is constructed from a plastic, glass, or ceramic material and acts as a carrier to the other portions, while portions of primary motion inducer 152 and/or secondary motion inducer 154 are made of an amorphous silicon or polycrystalline silicon material. Other portions of primary motion inducer 152 and/or secondary motion inducers, such as electrode elements, electrode pads, input/output pads, connective traces, etc., comprise a deposited metallization layer made from conductive trace materials such as copper, gold, platinum, palladium, graphite, etc.

This thin film technology described in association with FIG. 6 also can be used to implement one or more embodiments of biodevice 10 described in association with FIGS. 1–5 and 7–11.

Primary motion inducer 152 of transporter 150, as shown in FIG. 6, is configured for applying a traveling wave dielectrophoretic field to move cells through transporter 150 within a sorter assembly (such as sorter assembly 15 in FIG. 1). Accordingly, in one embodiment, primary motion inducer 152 has substantially the same attributes and features as transport mechanism 82 as implemented in electrode array 112 in FIG. 4.

Secondary motion inducer 154 is configured for applying a different force on cells to prevent their aggregation during their primary transport motion through transporter 150. Secondary motion inducer 154 of transporter 150 includes, but is not limited to, any electrically activatable device that is configurable as a thin film device and that imparts a translational, rotational, vibrational, or other motion in the cells at a magnitude that does not substantially disrupt the primary motion of the cells. In one embodiment, secondary motion inducer 154 comprises a piezoelectric device configured for applying an ultrasonic force or acoustic force on cells to impart the secondary motion to prevent cell aggregation.

Figure 7:
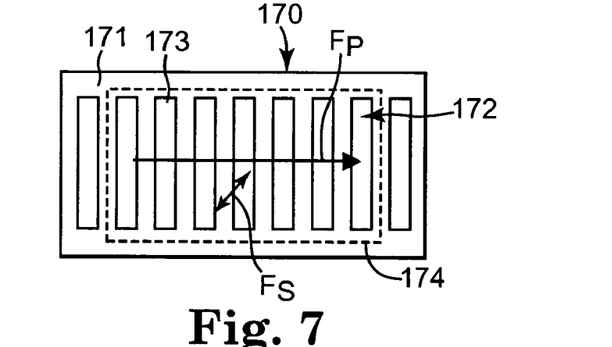
FIG. 7 is top plan view of a substrate of the cell transporter of FIG. 6, according to an embodiment of the present invention.

FIG. 7 is a top plan view of one embodiment of transporter 150 of FIG. 6 represented as transporter 170. As shown in FIG. 7, transporter 170 comprises surface 171 and electrode array 172 of elements 173 acting as primary motion inducer 152 (FIG. 6) while ultrasonic device 174 act as secondary motion inducer 154 (FIG. 6). In one embodiment, electrode array 172 operates in a manner substantially the same as electrode array 112 of FIG. 4 to permit application of a traveling wave dielectrophoretic field for applying the primary motion (represented by directional force arrow $F_P$). In particular, multiple electrode elements 173 are arranged into four sets of electrodes, with each set independently driven and corresponding to one of four separate signal channels.

In one embodiment, secondary motion imparter 174 comprises a piezoelectric device for applying an ultrasonic force (Fs) or acoustic force on cells 80. Accordingly, electrode array 172 applies a traveling wave dielectrophoretic field (via controller 19 in FIG. 2) to move cells in a direction of primary motion (as primary force $F_P$) while device 174 applies ultrasonic waves to impart secondary motion (e.g. rotational, vibrational, etc.) as secondary force $F_S$ to prevent aggregation of cells during their primary motion.

Figure 8:
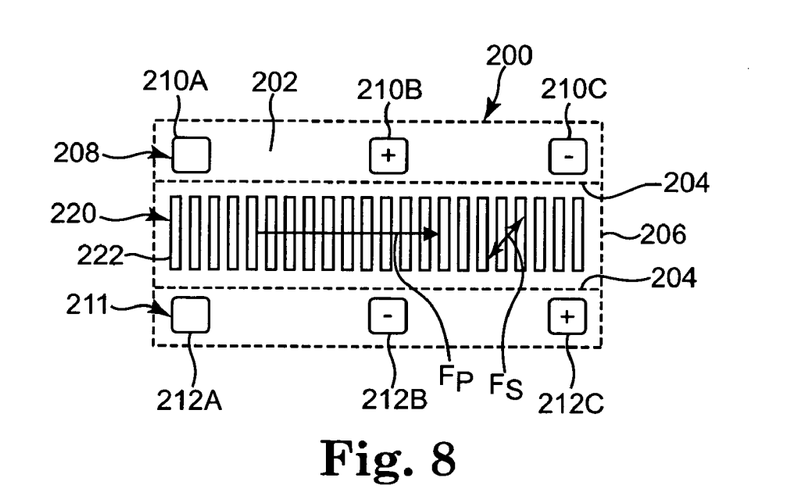
FIG. 8 is a top plan view of a substrate of another cell transporter, according to an embodiment of the present invention.

FIG. 8 is a sectional view of transporter 40 of FIG. 2 looking at a surface of second substrate 74, and illustrates one embodiment of transport mechanism 82 implemented as transporter 200 in second substrate 74. This embodiment of transporter 200 corresponds to the embodiment shown in FIG. 2 of anti-aggregation mechanism 84C (for imparting a secondary anti-aggregation motion on cells 80) being disposed alongside transport mechanism 82 for imparting a primary transport motion on cells 80.

As shown in FIG. 8, transporter 200 of a biodevice comprises surface 202 and walls 204 which define conduit 206. Transporter 200 also comprises first outer array 208 of electrode elements 210A, 210B, 210C, and second outer array 211 of electrode elements 212A, 212B, and 212C. In one embodiment, central electrode array 220 of elements 222 operates in a manner substantially the same as electrode array 112 of FIG. 4 to permit application of a traveling wave dielectrophoretic field for applying the primary motion (represented by directional force arrow $F_P$). In particular, multiple electrode elements 222 are arranged into four sets of electrodes, with each set independently driven and corresponding to one of four separate signal channels.

First and second outer electrode arrays 208, 211 are configured to impart the secondary motion on cells 80 (FIG. 2) with an electrorotational force ($F_S$) acting along the transport path defined by second substrate 74. Each element 210A–C, 212A–C of first and second outer electrode arrays 208, 211 is independently drivable by waveform generator 94 of controller 19 (FIGS. 1–2) to permit application of dielectrophoretic fields between adjacent electrode elements (210A–C, 212A–C) via progressive activation (or on/off cycling) to achieve or cause electrorotation in cells 80. Accordingly, transporter 200 of FIG. 8 applies both the primary motion and the secondary motion to move cells with minimal aggregation.

In one embodiment, electrode array 220 is not activated (or else omitted) and instead the primary motion is imparted via a fluid pressure drop along conduit 206 while electrode arrays 208 and 211 are still used to impart secondary motion of electro-rotation. In other embodiments, array 220 is activated or included, and used with or without a fluid pressure drop across second substrate 74 to impart the primary motion.

FIG. 8 is a representative section of a transport path of second substrate 74 of a biodevice 10. Consequently, transporter 200 may be longer than that shown, and accordingly, have more outer electrode elements in array 208 and 211 than the three electrode elements shown.

Figure 9:
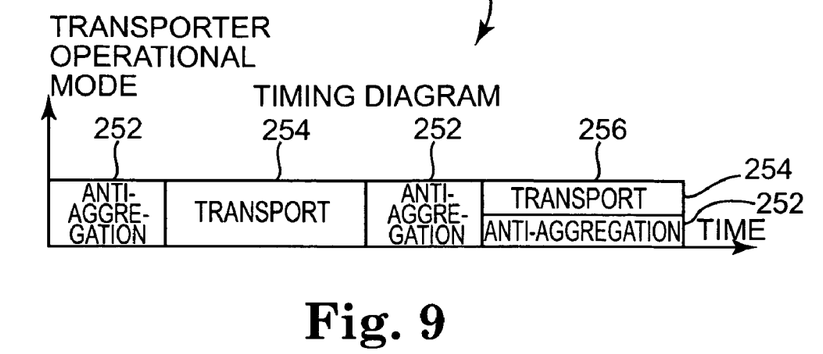
FIG. 9 is a diagram of a timing diagram of operation of a cell transporter, according to an embodiment of the present invention.

FIG. 9 illustrates a diagram of operation of controller 19 (FIGS. 1–2) during a transport time period on a biodevice. Controller 19, acts in part as a transport control unit, causing one or more first cycle(s) 252 of anti-aggregation movement to impart a secondary motion of cells on a transport path of a biodevice and one or more second cycle(s) 254 of transport movement to impart a primary motion of cells on a transport path of a biodevice. A third cycle 256, which comprises both anti-aggregation movement and transport movement of cells, simultaneously performs first cycle 252 and second cycle 254 so that both the primary motion and the secondary motion being imparted at the same time.

Different durations, sequences, combinations of the anti-aggregation cycle(s) 252 and transport cycle(s) 254 can be selected to optimize the desired transport and anti-aggregation effects. The operational modes represented by the diagram of FIG. 9 can be applied to devices and apparati described in association with FIGS. 1–8 and 10–11. Finally, additional aspects of anti-aggregation cycle 252 can be operated simultaneously, or alternately, with transport cycle 254, such as a centering cycle which is later described in more detail in association with FIG. 10.

While different sequences, combinations, and durations of the anti-aggregation effect and the transport effect can be used, all these cycles 252, 254, 256 taken together comprise a single transport time period in which cells are transported on biodevice 10 (without any sorting, isolation, testing, etc.) between other operational functions/stations of biodevice.

Figure 10:
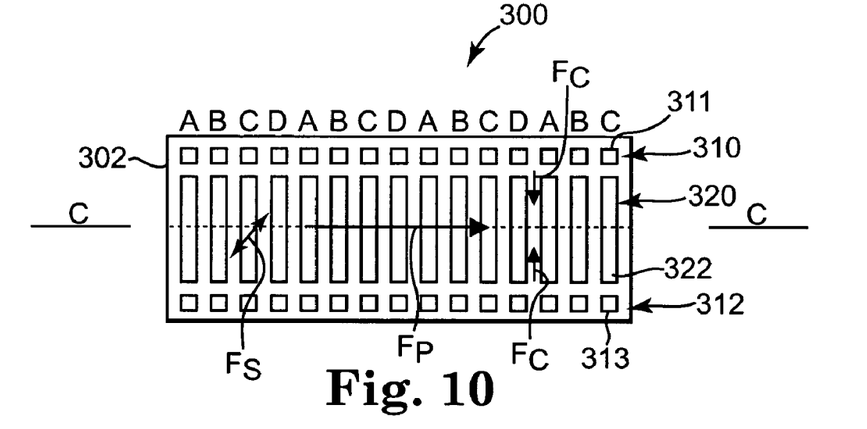
FIG. 10 is a top plan view of a substrate of another cell transporter, according to an embodiment of the present invention.

FIG. 10 is a sectional view of transporter 40 of FIG. 2 looking at a surface of second substrate 74, and illustrates one embodiment of transport mechanism 82 as transporter 300 in second substrate 74. This embodiment of transporter 300 corresponds to the embodiment of FIG. 2 in which anti-aggregation mechanism 84C (for imparting a secondary anti-aggregation motion on cells 80) is disposed alongside transport mechanism 82 for imparting a primary transport motion on cells 80.

FIG. 10 is a top view of transporter 300 of a biodevice 10. Transporter 300 comprises surface 302, first outer electrode array 310 of elements 311, second outer electrode array 312 of elements 313, and third central electrode array 320 of elements 322. Third central electrode array 320 applies a traveling wave dielectrophoretic field to move cells in a primary motion along transport path (represented by directional arrow $F_P$). In one embodiment, third central electrode array 320 operates in a manner substantially the same as electrode array 112 of FIG. 4 to permit application of a traveling wave dielectrophoretic field for applying the primary motion (represented by directional force arrow $F_P$). In particular, multiple electrode elements 322 are arranged into four sets of electrodes, with each set independently driven and corresponding to one of four separate signal channels.

Locating first and second electrode arrays 310, 312 adjacent to and substantially in the same plane as central electrode array 320 corresponds to a combination of transport mechanism 82 and anti-aggregation mechanism 84C of transporter 40 of biodevice 10 of FIG. 2.

First and second outer electrode arrays 310, 312 can be operated in three different modes. Each mode can be used alone or in combination with central electrode array 320.

In a first mode, first and second outer electrode arrays 310, 312 apply a dielectrophoretic field for inducing electrorotation as the secondary motion on cells 80. In one embodiment, outer electrode arrays 310, 312 operate in a manner substantially similar to electrode arrays 208, 211 as previously described in association with FIG. 8. In this first operational mode, first and second outer electrode arrays 310, 312 do not contribute to generating the traveling wave dielectrophoretic field for imparting the primary motion. However, when operating in the first mode, first and second outer electrode arrays 310, 312 can operate simultaneous with the application of the traveling wave by central electrode array 320.

In a second mode, first and second outer electrode arrays 310, 312 act in concert with third central electrode array 320. In one embodiment, as shown in FIG. 10, each element 322 of central electrode array 320 corresponds to one of elements 311, 313 of outer electrode arrays 310, 312, respectively. When one of elements 322 is activated as part of a traveling wave, substantially similar to the manner described for electrode array 112 of FIG. 4, then corresponding elements 311, 313 of outer electrode arrays 310, 312 are activated simultaneously with central element 322 so that all three electrode elements 322, 311, 313 act together as a signal unit for a single channel (e.g., channel A) of four channel signal set (e.g., channels A, B, C, D) to impart the traveling wave.

In a third mode, first and second outer electrode arrays 310, 312 are operated independently of central electrode array 320 to create a negative dielectrophoretic field (producing a centering force $F_C$) that is biased alternately (e.g., 180 degrees out of phase) to drive cells 80 away from outer walls of the conduit, i.e. toward a center of the conduit. This centering effect prevents the cells from adhering to a wall of the conduit defining the transport path. This alternately biased electric field is generated by wave generator 94 of controller 19, shown in FIG. 2. This centering effect focuses the cells back toward a center of the transport path, which contributes to the primary motion of transport by keeping the cells in a central portion of the traveling wave dielectrophoretic field and contributes to the secondary motion of by preventing cell adhesion to the walls of the transport path.

Figure 11:
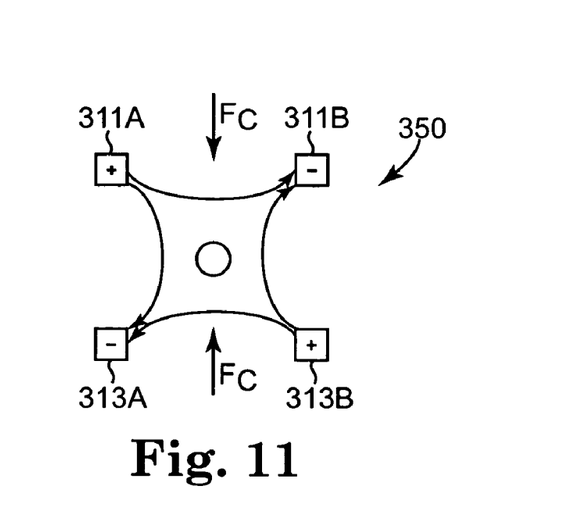
FIG. 11 is a schematic illustration of a cell centering mechanism, according to an embodiment of the present invention.

FIG. 11 schematic illustrates a portion of electrode arrays 310 and 312 operating together in the third mode to achieve a centering force. As shown in FIG. 11, in this mode, adjacent elements 311A, 311B of electrode array 310 and adjacent elements 313A, 313B of electrode array 312 are shown out of phase relative to one another. In addition, element 311A is out of phase by 180 degrees from element 313A, and element 311B is out of phase by 180 degrees from element 313B. By alternating these phases in cycles, the respective electrode elements create a negative dielectrophoretic field that tends to move the cells to a center position between the respective electrode elements.

Various combinations of applying the first, second and third operational modes for outer electrode arrays 310, 312 are used to achieve different effects. In one embodiment, outer electrode arrays 310, 312 are used in the second mode to assist central electrode array 320 in applying a traveling wave dielectrophoretic field to impart a primary motion on cells. Then, while the central electrode array 320 is still applying a traveling wave, outer electrode arrays 310, 312 are switched to the first mode or third mode to apply a secondary motion to the cells. Moreover, controller 19 (FIG. 2) can alternate between the first and third modes, to alternately apply electrorotation and centering, while the central electrode array 320 maintains the traveling wave. Accordingly, in this embodiment a single electrode arrangement (both outer electrode arrays 310, 312 and central electrode array 320) generates both the primary motion and the secondary motion on the cells.

In other embodiments, central electrode array 320 can be activated alternately with outer electrode arrays 310, 312, similar to the operational cycles shown in FIG. 9. In particular, outer electrode arrays 310, 312 are activated for an anti-aggregation cycle while central electrode array 320 is dormant. Next, outer electrode arrays 310, 312 are deactivated to stop the anti-aggregation cycle, and central electrode array 320 is activated for a transport cycle. This alternating pattern can be repeated and/or changed in order. Finally, cycle 256 of the timing diagram of FIG. 9 shows simultaneous operation of anti-aggregation cycle and transport cycles which can be implemented at any point by activating outer electrode arrays 310, 312 in one or more of the first and third modes to impart the secondary anti-aggregation motion while central electrode array 320 applies a traveling wave to impart the primary transport motion on the cells.

Embodiments of the present invention provide for relatively aggregation-free transport of cells and particles across a portion of a biodevice between sorting operations and other functions of the biodevice. This minimally-aggregation cell transport is achieved through dual application of a primary motion and a secondary motion in various combinations.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A biodevice comprising:
   an array of operative stations with each respective operative station configured for performing an operation on cells; and
   a transporter configured for transporting cells during a transport time period, the transporter in fluid communication with at least one of the respective operative stations and independent of and separate from the at least one respective operative station, the transporter comprising:
      a motion-inducing apparatus configured to induce transportation of the cells along a transport path of the biodevice between the respective operative stations of the biodevice, the apparatus comprising an electrode arrangement configured to apply a non-uniform electric field to the cells; and
      a transport control unit coupled to the motion-inducing apparatus to control transportation of the cells and providing control signals to the motion-inducing apparatus during the transport time period to:
      induce a primary motion of the cells to drive transportation of the cells along the transport path; and
      induce a secondary motion of the cells to discourage aggregation of the cells during transportation of the cells on the transport path without performing, via the at least one respective operative station, an operation on the cells.

2. The biodevice of claim 1 wherein the transport control unit of the transporter is configured to operate the motion-inducing apparatus such that the primary and secondary motion occurs at least one of simultaneously during the transport time period and alternately during the transport time period.

3. The biodevice of claim 1 wherein the motion-inducing apparatus of the transporter includes a first apparatus that induces the primary motion and a second apparatus that induces the secondary motion.

4. The biodevice of claim 3 wherein the first apparatus and the second apparatus are vertically disposed with respect to one another.

5. The biodevice of claim 4 wherein the second apparatus is disposed on a first substrate and the first apparatus is disposed on a second substrate, with the first and second substrate being spaced from one another so that the transport path extends generally parallel between the first apparatus and the second apparatus.

6. The biodevice of claim 5 wherein the first apparatus comprises a first portion of the electrode arrangement, which is configured to impart a traveling wave in the non-uniform electric field.

7. The biodevice of claim 6 wherein the second apparatus comprises a second portion of the electrode arrangement and comprises a plurality of elongate electrode elements extending along a length of the transport oath and arranged generally parallel to the direction of primary motion along the transport path, the electrode elements spaced apart from each other and extending generally parallel to a longitudinal axis of the transport path, wherein the elongate electrode elements are configured to apply a non-traveling wave, spatially varying electric field between the electrode elements to define a plurality of generally parallel and independent channels in the transport path between the elongate electrode elements to substantially prevent cell aggregation along the transport path via maintaining the cells in the different respective independent channels.

8. The biodevice of claim 3 wherein the second apparatus is a plurality of electrode elements disposed on at least one of a top substrate and a bottom substrate, with the plurality of electrode elements including a first outer set and a second outer set of electrode elements, with the first outer set disposed on a first side of the transport path and the second outer set disposed on a second side of the transport path, and wherein the electrode elements within each of the respective first outer sets and second outer sets are longitudinally spaced from each other along the transport path.

9. The biodevice of claim 8 wherein the first and second outer sets of electrode elements are disposed on the bottom substrate, and the electrode arrangement further comprises a central electrode array of electrode elements that is disposed underneath the transport path centrally between the first outer set and the second outer set of electrode elements.

10. The biodevice of claim 9 wherein each electrode element of the central electrode array corresponds to, and is aligned generally parallel to, one electrode element of each of first outer set and second outer set of electrode elements, which are located laterally relative to each electrode element of the central electrode array on opposite sides of the corresponding electrode element of the central electrode array.

11. The biodevice of claim 10 wherein the transport control unit operates the first and second outer sets of electrode elements in a mode that applies a traveling wave in the non-uniform electric field in cooperation with the central electrode array.

12. The biodevice of claim 10 wherein the transport control unit operates the first and second outer sets of electrode elements in a mode that applies the non-uniform electric field to deliver the secondary motion as an electrorotational force on the cells.

13. The biodevice of claim 10 wherein the transport control unit operates the first and second outer sets of electrode elements in a mode that applies the non-uniform electric field within the transport path to the cells to move the cells toward a center of the transport path.

14. The biodevice of claim 10 wherein the transport control unit of the transporter operates the first and second outer sets of electrode elements in at least two of three modes including:
   a first mode that applies a first traveling wave in the non-uniform electric field in cooperation with the central electrode array;
   a second mode that applies a second non-uniform electric field to deliver the secondary motion as an electrorotational force on the cells; and
   a third mode that applies a third non-uniform electric field within the transport path to the cells to move the cells toward a center of the transport path.

15. The biodevice of claim 10 wherein all the outer electrode elements and the central electrode array operate as the first apparatus in a first time period, and wherein in a second time period, only the central electrode array operates as the first apparatus.

16. The biodevice of claim 1 wherein the primary motion is induced by a fluid pressure flaw drop along the transport path.

17. The biodevice of claim 1 wherein the electrode arrangement of the motion-inducing apparatus is configured to apply the non-uniform electric field as a temporally varying non-uniform electric field.

18. The biodevice of claim 1 wherein the array of operative stations comprises at least one of a cell testing station, a cell filter station, a cell sorting station, and a cell collecting station.

19. A transporter of a biodevice for transporting cells during a transport time period, the transporter comprising:
   a motion-inducing apparatus configured to induce transportation of the cells along a transport path of the biodevice between other operative positions of the biodevice, the apparatus comprising an electrode arrangement configured to apply a non-uniform electric field to the cells and the motion-inducing apparatus including a first apparatus and a second apparatus with the first apparatus being vertically disposed relative to the second apparatus; and
   a transport control unit coupled to the motion-inducing apparatus to control transportation of the cells and providing control signals to the motion-inducing apparatus during the transport time period to:
   induce a primary motion of the cells, via the first apparatus, to drive transportation of the cells along the transport path; and
   induce a secondary motion of the cells, via the second apparatus, to discourage aggregation of the cells during transportation of the cells,
   wherein the first apparatus is overlaid onto the second apparatus in a single substrate, with both the first apparatus and the second apparatus disposed underneath the transport path, and wherein the second apparatus comprises a piezoelectric device configured to apply a vibratory force to the cells for preventing aggregation of the cells during the transport time period.

20. An apparatus for moving cells on an electronic biodevice between operative stations on the biodevice during a transport time period, the apparatus comprising:
   means for imparting a primary motion of the cells on the biodevice a cell transport path to transport the cells between the operative stations on the biodevice, and a secondary motion of the cells to substantially prevent aggregation of the cells during the cell transport on the cell transport path, wherein the means for imparting is independent of and separate from the operative stations that are in fluid communication with the cell transport path; and means for controlling the means for imparting, via control signals, to selectively activate the primary motion to move the cells along the cell transport path and to selectively activate the secondary motion to maintain substantially aggregation-free transport of the cells without sorting the cells along the cell transport path during the transport time period.

21. The apparatus of claim 20 wherein the means for imparting a primary motion of the cells comprises an electrode array having a first portion configured to apply a traveling wave dielectrophoretic field.

22. The apparatus of claim 21 wherein the electrode array comprises a second portion configured to apply at least one of: (1) the traveling wave dielectrophoretic field along with the first portion of the electrode array; and (2) a dielectrophoretic field configured for imparting the secondary motion, wherein the second portion of the electrode array produces the secondary motion with the dielectrophoretic field via at least one of: (1) an electrorotative effect on the cells that rotates the cells; and (2) a centering effect on the cells that moves the cells toward a center of the transport path.

23. The apparatus of claim 20 wherein the operative stations of the biodevice comprise at least one of a cell testing station, a cell filter station, a cell sorting station, and a cell collecting station.

24. An apparatus for moving cells on an electronic biodevice during a transport time period, the apparatus comprising:

means for imparting a primary motion of the cells on the biodevice to transport the cells between stations on the biodevice, and a secondary motion of the cells to substantially prevent aggregation of the cells during the cell transport, the means for imparting a primary motion of the cells comprising an electrode array having a first portion configured to apply a traveling wave dielectrophoretic field and the electrode array including a second portion configured to apply at least one of: (1) the traveling wave dielectrophoretic field along with the first portion of the electrode array; and (2) a dielectrophoretic field configured for imparting the secondary motion, wherein the second portion of the electrode array is configured to produce the secondary motion with the dielectrophoretic field via at least one of: (1) an electrorotative effect on the cells that rotates the cells; and (2) a centering effect on the cells that moves the cells toward a center of the transport path, wherein the means for imparting the secondary motion of the cells comprises a piezoelectric device disposed below the first portion of the electrode array and is configured to apply an ultrasonic force on the cells; and means for controlling the means for imparting, via control signals, to selectively activate the primary motion and the secondary motion to maintain substantially aggregation-free transport of the cells during the transport time period.

25. An apparatus for moving cells on an electronic biodevice during a transport time period, the apparatus comprising:

means for imparting a primary motion of the cells on the biodevice to transport the cells between stations on the biodevice, and a secondary motion of the cells to substantially prevent aggregation of the cells during the cell transport, the means for imparting a primary motion of the cells comprising an electrode array having a first portion configured to apply a traveling wave dielectrophoretic field; and means for controlling the means for imparting, via control signals, to selectively activate the primary motion and the secondary motion to maintain substantially aggregation-free transport of the cells during the transport time period, wherein the means for controlling the means for imparting comprises a transport control unit configured to apply the primary motion and the secondary motion in alternating cycles, wherein the primary motion is produced by at least one of: (1) a fluid flow pressure drop; and (2) the traveling wave dielectrophoretic field applied via the first portion of the electrode array, and wherein the secondary motion is produced via at least one of a negative dielectrophoretic field and an ultrasonic force wave.

26. The apparatus of claim 25 wherein the transport control unit is configured to also apply the primary motion and the secondary motion simultaneously.

* * * * *

UNITED STATES PATENT AND TRADEMARK OFFICE
CERTIFICATE OF CORRECTION

PATENT NO. : 7,160,425 B2
APPLICATION NO. : 10/808897
DATED : January 9, 2007
INVENTOR(S) : Winthrop D. Childers et al.

It is certified that error appears in the above-identified patent and that said Letters Patent is hereby corrected as shown below:

In column 13, line 19, in Claim 7, delete "oath" and insert -- path --, therefor.

In column 14, line 22, in Claim 16, delete "flaw" and insert -- flow --, therefor.

In column 14, line 36, in Claim 19, delete "positions" and insert -- portions --, therefor.

In column 14, line 65, in Claim 20, after "biodevice" insert -- along --.

In column 15, line 25, in Claim 22, delete "one of;" and insert -- one of: --, therefor.

Signed and Sealed this

Thirty-first Day of March, 2009

JOHN DOLL
*Acting Director of the United States Patent and Trademark Office*